(12) United States Patent
Krietzman (10) Patent No.: US 11,457,667 B2
(45) Date of Patent: Oct. 4, 2022

(54) CHILD RESISTANT VAPORIZER DEVICES

(71) Applicant: Mark Krietzman, Palos Verdes Estates, CA (US)

(72) Inventor: Mark Krietzman, Palos Verdes Estates, CA (US)

(*) Notice: Subject to any disclaimer, the term of this patent is extended or adjusted under 35 U.S.C. 154(b) by 594 days.

(21) Appl. No.: 16/457,312

(22) Filed: Jun. 28, 2019

(65) Prior Publication Data

US 2020/0022411 A1 Jan. 23, 2020

Related U.S. Application Data

(60) Provisional application No. 62/698,422, filed on Jul. 16, 2018, provisional application No. 62/691,609, filed on Jun. 29, 2018.

(51) Int. Cl.
| | | |
|---|---|---|
| A24F 13/00 | (2006.01) | |
| A24F 17/00 | (2006.01) | |
| A24F 25/00 | (2006.01) | |
| A24F 40/49 | (2020.01) | |
| A61M 11/04 | (2006.01) | |

(52) U.S. Cl.
CPC ............ *A24F 40/49* (2020.01); *A61M 11/042* (2014.02); *A61M 2205/276* (2013.01)

(58) Field of Classification Search
CPC ....... A24F 40/10; A24F 40/49; A61M 11/042; A61M 15/0026; A61M 15/08; A61M 2205/276
See application file for complete search history.

(56) References Cited

U.S. PATENT DOCUMENTS

| | | | | |
|---|---|---|---|---|
| 11,007,546 B2* | 5/2021 | Hohmann | ............ | B05B 11/0032 |
| 2002/0179179 A1* | 12/2002 | Volpenheim | ............ | B65D 35/40 |
| | | | | 141/381 |
| 2013/0218066 A1* | 8/2013 | Duquet | .................. | A45D 34/04 |
| | | | | 604/20 |
| 2014/0097207 A1* | 4/2014 | Szymiczek | ......... | B05B 11/0032 |
| | | | | 222/153.13 |
| 2015/0284177 A1* | 10/2015 | Patil | ...................... | A61M 15/08 |
| | | | | 222/153.04 |
| 2015/0306617 A1* | 10/2015 | Olegnowicz | ........ | B05B 11/0044 |
| | | | | 222/1 |
| 2017/0360092 A1* | 12/2017 | Althorpe | ................. | F22B 1/284 |
| 2018/0030974 A1* | 2/2018 | Cosgarea | .............. | F04B 39/123 |
| 2018/0140001 A1* | 5/2018 | Gabbay | ................ | A24B 15/167 |
| 2020/0138117 A1* | 5/2020 | Rosser | .................. | A61M 15/06 |
| 2020/0156826 A1* | 5/2020 | Kilduff | ................ | B65D 43/162 |
| 2020/0377280 A1* | 12/2020 | Pace | .................. | B65D 43/0225 |

* cited by examiner

*Primary Examiner* — Abdullah A Riyami
*Assistant Examiner* — Thang H Nguyen
(74) *Attorney, Agent, or Firm* — Mark Krietzman (57) ABSTRACT

Exemplars include controls, limits or the selective stopping of vapor flow through a vaporizer cartridge and tip. A blocking member such as a deformable squeeze valve formed as at least a portion of the tip or a plunger formed within a cap having ports which fluidly communicate from the outside of the cap to the inside which is selectively moved in and out of an outlet to limit or prevent vapor flow.

11 Claims, 9 Drawing Sheets

CHILD RESISTANT VAPORIZER DEVICES

RELATED APPLICATION

This application claims the benefit of Applicant's United States ("U.S.") Provisional Patent Application Ser. No. 62/691,609 filed Jun. 29, 2018 TAMPER RESISTANT VAPORIZER DEVICES and 62/698,422 filed Jul. 16, 2018 entitled "SAFER VAPORIZER DEVICES" the entirety of which are both incorporated by reference herein in as if set forth in their entirety.

BACKGROUND OF THE DISCLOSURE

Field of the Disclosure

The present disclosure relates generally to control of fluid flow through a vaporizer cartridge.

Related Art

Vaporizers for many essential oils have become common place. The range of aromatherapy oils is very large with different oils vaporizing at different temperatures. These devices may be a simple as inhale and a battery supply immediately heats a coil or other heating element to heat the oil and produce vapor. Other device may require a sequence of button pushing or switch flipping.

*Cannabis* extracted oils are also commonly found in such cartridges. *Cannabis sativa* contains over 421 different chemical compounds, including over 60 cannabinoids. Cannabinoid plant chemistry is far more complex than that of pure THC, and different effects may be expected due to the presence of additional cannabinoids and other chemicals. Eighteen different classes of chemicals, including nitrogenous compounds, amino acids, hydrocarbons, carbohydrates, terpenes, and simple and fatty acids, contribute to the known pharmacological properties of *Cannabis*.

*Cannabis*, for example has a narrow range at which it can be heated to release "THC" (Tetrahydrocannabinol (THC), or more precisely its main isomer (−)-trans-$\Delta^9$-tetrahydrocannabinol) and CBDs (Cannabidiol loosely referring to as many as 85 identified compounds in *Cannabis*) chemicals as vapor without burning the organic material and adding non-THC and CBD material to the inhalation gases.

Children are curious and will imitate adult use or simple explore. It is therefore a desideratum to have child resistant vaporizer.

DISCLOSURE

In the following description of examples of implementations, reference is made to the accompanying drawings that form a part hereof, and which show, by way of illustration, specific implementations of the present disclosure that may be utilized. Other implementations may be utilized and structural changes may be made without departing from the scope of the present disclosure.

Vaporizer batteries, control circuits and the like are known. This disclosure should be interpreted broadly and is a mechanical solution for a plethora of vaporizer devices to discourage, frustrate or prevent child use. Title 16 of the Code of Federal Rules (CFR) 1700.15 describes safety packaging for poisons and the need for child resistant packaging. That governmental code is hereby referenced and incorporated by this reference as if fully set forth herein. In relevant part is sets standards to prevent accidental or misuse by children. It also has specific guideline for aerosols.

Aspects of a tamper resistant vaporizer cartridge include a method of selective blocking and unblocking vapor flow through a tip, the method controls vapor output of a vaporizer cartridge through a fluidly connected tip by blocking said vapor flow. Cartridges are configured to mate with a power supply at a first end and have a vapor pathway at a second end; the vapor pathway is configured to mate with a tip having a proximal end, a distal end and a vapor outlet therethrough forming a fluid pathway from the vapor outlet to the vapor pathway; opening the fluid pathway through the tip by moving a vapor blocking cap axially from the second end towards the vapor blocking cap's top thereby displacing one or more flexible fingers formed at the distal end of the cap over a radial interference member (formed on the tip to remove the vapor blocking cap from the tip; and, wherein the one or more flexible fingers formed on the vapor blocking cap is configured to rest below the radial interference member; and, wherein a predetermined force is required to displace the finger over the interference member.

The tip is a control means for a vaporizer cartridge which is configured to receive power from a power supply at a first end and with a vapor pathway at a second tip connection. For a disposable vaporizer system the battery power supply and cartridge may be an integrated unit. The control tip taught herein is equally applicable for such an integrated unit and such a unit is anticipated hereby. A wide variety of vaporizer configuration exist and it is not possible nor required to detail every possible configuration of same in this disclosure. Those of ordinary skill in the art will recognize the tip control of vapor flow as being applicable to same.

Aspects of a tamper resistant vaporizer cartridge include a device and method of selective blocking and unblocking vapor flow through a tip, the method involving selective blocking and unblocking vapor flow through a tip. The tip is the outlet end of a pen style vaporizer. The vaporizer provides power to a cartridge thereby heating an extract and producing vapor Aspects of tips having a body, top end, bottom end and flexible side walls surrounding a fluid pathway are taught. In such a soft or flexible tip at least a portion of the tip is made of the pliant or soft material. A first half pathway is formed which is fluidly connected to a vapor outlet through the distal end of the tip and a second half pathway is fluidly connected to an inhalation outlet. A valve passage is formed of a deformable wall region that is flat at rest (and therefore not open) forming a valve in a sealed state; and, whereby squeezing the side walls of the soft tip portion with a predetermined force deforms and opens the squeeze valve thereby allowing vapor produced by a cartridge fluidly connected to the tip to will flow through the first and second half pathways. The predetermined force should be a force that is too great for at least ninety percent of five year old to overcome. More preferably the predetermined force is a force that is too great for at least ninety-five percent of five year old to overcome.

Aspects of a tamper resistant vaporizer cartridge include a device and method of selective blocking and unblocking vapor flow through a tip are disclosed. A vaporizer cartridge configured to receive power from a power supply and with a vapor pathway and connection is connected to a valve tip via the connection. The valve tip has a body has a proximal end with an outlet fluidly connected to a valved pathway, at least one force limiting rib (FLR), a valve stem guide and a series of fluid connections therethrough. The distal end of the tip has a vapor outlet (130) connected to the outlet. A valve stem is configured to shut on and off vapor flow through the tip. The valve stem has an elongated body, a stem proximal head, a distal stem end, a valve connect configured to mate within the stem guide and block the fluid pathway in a first configuration and unblock the fluid pathway in a second configuration. The stem proximal head which is limited from turning to align the valve connect to the second configuration by the at least one FLR; and the stem proximal head can be turned past the FLR be a predetermined amount of rotational force or torque.

The predetermined force is a force that is too great for at least ninety percent of five year old to overcome. Preferably the predetermined force is a force that is too great for at least ninety-five percent of five year old to overcome.

Aspects of a tamper resistant vaporizer cartridge include a device and method of selective blocking and unblocking vapor flow through a tip are disclosed. A vaporizer cartridge configured to receive power from a power supply and with a vapor pathway and connection is connected to a valve tip via the connection. The tip has a vapor outlet formed therethrough, a proximal end and a distal end. The distal end is configured to be in fluid communication via the vapor outlet with the cartridge vapor pathway. A fluid pathway through the tip is opened and closed by moving a vapor blocking cap axially from the second end towards the vapor blocking cap's top thereby displacing one or more flexible fingers formed at the distal end of the cap over a radial interference member formed on the tip to remove the vapor blocking cap from the tip. Wherein the one or more flexible fingers formed on the vapor blocking cap is configured to rest below the radial interference member and, wherein a predetermined force is required to displace the finger over the interference member.

Aspects of a tamper resistant vaporizer cartridge include a device and method of selective blocking and unblocking vapor flow through a tip are disclosed. A vaporizer cartridge configured to receive power from a power supply and with a vapor pathway and connection is connected to a valve tip via the connection. The tip has a series of outlets formed therethrough configured to selectively be in fluid communication. The tip has a proximal end with an outlet and a distal end to form a fluid pathway from the cartridge to the tip. The second end forming a fluid pathway from the vapor outlet to the vapor pathway. The opening of the fluid pathway through of the tip is accomplished by pulling a barrier cap axially from the second end towards the top of the barrier cap thereby displacing one or more flexible fingers formed at the distal end of the barrier cap from a first at rest position in a first catch over an interference member and into a second position in a second catch thereby unblocking the outlet by moving a plunger extending downward axially from the barrier cap top and within the barrier cap from blocking the outlet. Unblocking the outlet allows vapor to flow through the vapor flow guide (VFG) formed by the barrier cap and be drawn out of one or more inhalation ports. A predetermined force is required to displace the finger over the interference member thereby limiting access to the vapor for persons such as children who lack the strength or dexterity to move the barrier cap.

In some instances the predetermined force is a force that is too great for at least ninety percent of five year old to overcome. In some instances the predetermined force is a force that is too great for at least ninety-five percent of five year old to overcome. In some instances the second catch has at least one shaped surface configured to prevent removal of the at least one flexible finger by the force necessary to move the fingers from the first catch over the interference member and into the second catch. To close the flow of vapor the method involves pressing on the barrier cap towards the distal end of the vaporizer cartridge wherein the fingers move from the second catch to the first catch and block the fluid pathway.

Aspects of a tamper resistant vaporizer cartridge include a device and method of selective blocking and unblocking vapor flow through a tip are disclosed. A vaporizer cartridge configured to receive power from a power supply and with a vapor pathway and connection is connected to a valve tip via the connection. The tip has a series of outlets cooperating to selectively form a blockable fluid pathway. A tip having a vapor outlet, proximal end with an outlet and a distal end connect to the second end (which produces a vapor stream upon heating) of a cartridge, That connection forms a fluid pathway from the vapor outlet to the vapor pathway. Opening the fluid pathway through of the tip is accomplished by rotating a control cap displacing one or more flexible feet formed at the distal end of the control cap from a first at rest position in a deep catch formed in the tip and into a second position on a shallow catch and pulling the valve cap upward towards its top thereby unblocking the outlet by moving a plunger extending downward axially from the control cap top and within the control cap from blocking the outlet. Accordingly, vapor can flow through the cap and be drawn out of one or more inhalation ports. In some instances a predetermined force is required to displace the one or more feet from the deep catch.

To limit use by children of the above described devices in some instances the predetermined force is a force that is too great for at least ninety percent of five year old to overcome. To limit use by children of the above described devices in some instances the predetermined force is a force that is too great for at least ninety-five percent of five year old to overcome.

In some instances to close the vapor flow through the tip the user or operator rotates the cap in reverse and said rotation directs the feet and toes back into the deep catch wherein the one or more feet move from the shallow catch to the deep catch and moves the plunger to block the fluid pathway.

Aspects of a tamper resistant vaporizer cartridge include a device and method of selective blocking and unblocking vapor flow through a tip are disclosed. A vaporizer cartridge configured to receive power from a power supply and with a vapor pathway and connection is connected to a valve tip via the connection. The tip has a vapor outlet, a proximal end with an outlet and a distal end and a first catch formed radially around the distal end of the tip. Adjacent to the first catch is a second catch formed radially around the distal end of the tip. An interference member is formed between the first and second catches configured to cooperate with the flexible legs of the cap to provide force control. A barrier cap configured to mount over the tip in a movable fashion has a top and a distal end. A plunger which is used to control vapor flow extends downward axially from the top within the barrier cap. At least one flexible leg formed at the distal end of the barrier cap configured to latch with the catches. The fluid pathway for vapor is opened through the barrier cap from the tip through one or more inhalation ports when the cap is raised from one catch to another and closed off by the reverse movement of legs in catches. A predetermined force is required to displace the leg over the interference member.

FIGURES

The invention may be better understood by referring to the following figures. The components in the figures are not necessarily to scale, emphasis instead being placed upon illustrating the principles of the invention. In the figures, like reference numerals designate corresponding parts throughout the different views.

All descriptions and callouts in the Figures and all content therein are hereby incorporated by this reference as if fully set forth herein.

FURTHER DISCLOSURE

Disclosed herein are aspects of devices, methods and systems of tamper resistant modules for an electronic vaporizer cartridge.

Figure 1:
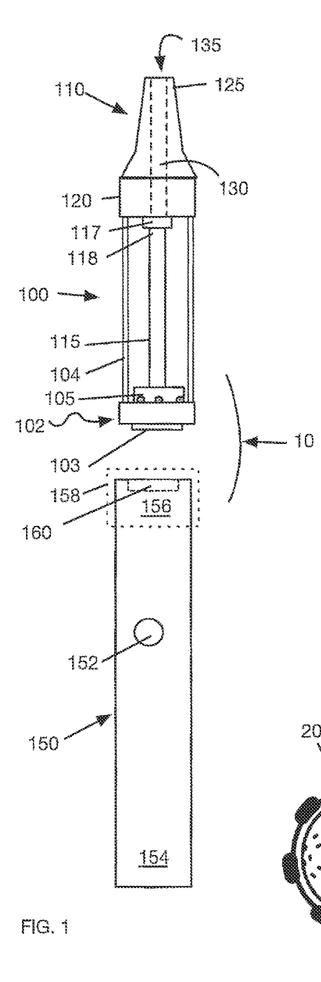
FIG. 1 is an component view of a pen type vaporizer for extract.
Figure 2A:
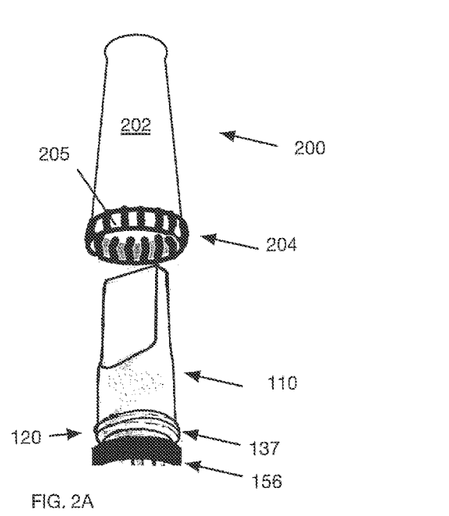
FIGS. 2A-2D illustrates aspects of a snap on tamper resistant flow control vaporizer cartridge.
Figures 2B, 2D:
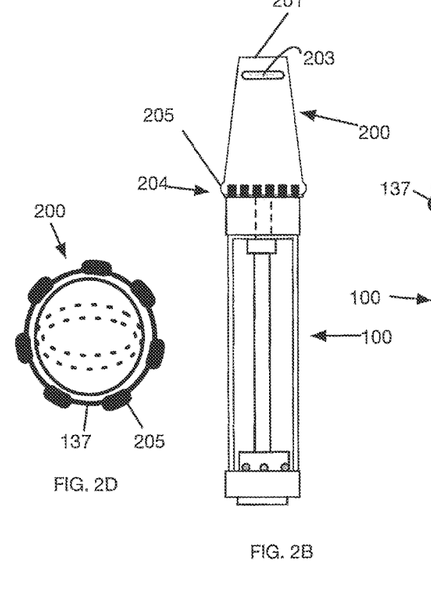
Figure 2C:
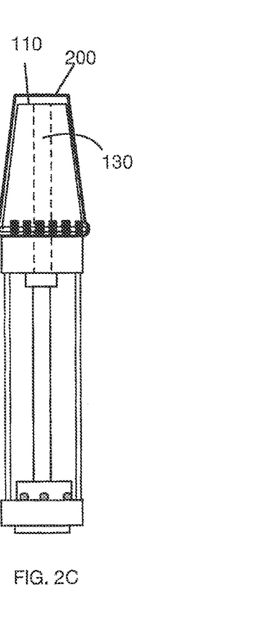

FIG. 1 illustrates a traditional vaporizer system 10 with replaceable cartridge 100. Body 150 containing a power supply and controller (not shown) has an on/off switch 152 accessible on the body a distal end 154 and a proximal end 156. A cartridge interface 158 is configured at one end to mount to the replaceable cartridge 100. Cartridges are shown as linear but those of ordinary skill in the rat will recognize that a squat or square cartridge with a inhalation outlet is also within the scope of this disclosure. The cartridge has a first end 102 configured to mate with the cartridge interface 158. At the first end is a power connection 103 configured to electrically connect to the power coupling 160 on the body. The interface connection may be friction fit or preferably via threaded fitting.

A cylindrical tube 104 is connected to the first end on the opposite side as the power connection 103. Within the cylindrical tube is an electrical heating element 105 containing a heater and connected to a vapor pathway 115 which may have a tip gasket 117 at its tip connection 118. The tip has a distal end 120 which connects with the connection end of the fluid pathway and with the tube 104 and it has a proximal end 125. A vapor inlet/pathway 130 is formed axially in the tip from the distal end to the proximal end and is configured to connect to the vapor pathway to form a fluid pathway from the cartridge heater to an inhalation port 135 at the top of the proximal end of the tip.

FIGS. 2A through 2D illustrate aspects of a snap on tamper resistant tip cover having top 201 blocking one end of a hollow body 202 forming a vapor blocking cap 200 configured to mate over the tip 110. Optionally, near the top 201 one or more of a texture, extension, bump, divot, outcropping or indentation 203 may be formed as a finger, finger nail or bite grasp. At the distal end 204 of the vapor blocking cap are one or more flexible fingers 205. The flexibility is a matter of material choice. Plastics, resins and thin metals may be used. Materials with the sufficient resiliency to form a flexible movable structure that can move radially when displaced are adequate. Some describe these materials as living hinges formed in a single molded plastic piece with adequate resiliency to move sufficient time to provide a viable tamper resistant cover for a predetermined number of attachments and removals. Spring steel, Polypropylene, polyethylene, nylon, polycarbonate, and the like may be used. The finger(s) 205 form a shaped latch configured to connect into or over a radially interference member 137 formed around the distal end 120 of the tip.

Figure 3A:
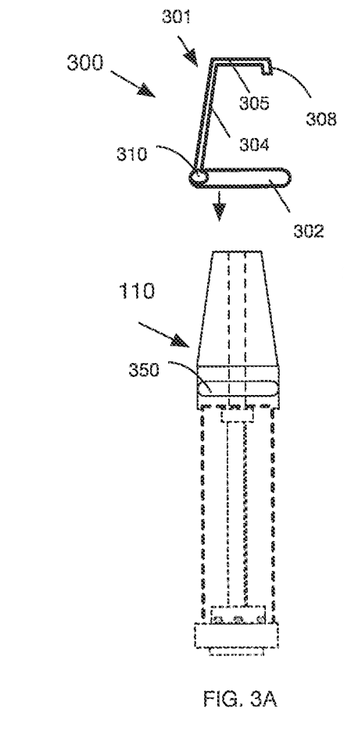
FIGS. 3A to 3C show an assembly view and a sequence of use view of a flip top tamper resistant flow control vaporizer cartridge.
Figures 3B, 3C:
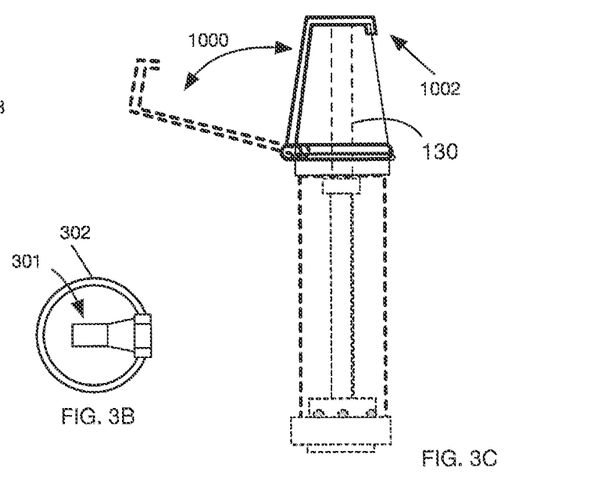

FIGS. 3A through 3C show aspects if a collared flip top 300. The flexible arm 301 is affixed to a ring shaped collar 302 that firmly mates with an interface 350 on the tip. The mating may be pressure fit, latch and catch, sonic weld or adhesive. The collar may be a partial circle. The flexible arm has a vertical member 304 a cross member 305 and a lip 308 which are a single piece that is configured to tightly fit over the tip. A pivot 310 is formed between the flexible arm and the collar allowing rotation along the path of arrow 1000. By applying force at the lip 208 along the line of arrow 1002 the flip top 300 may be displaced from blocking the vapor inlet/pathway 130.

Figure 4:
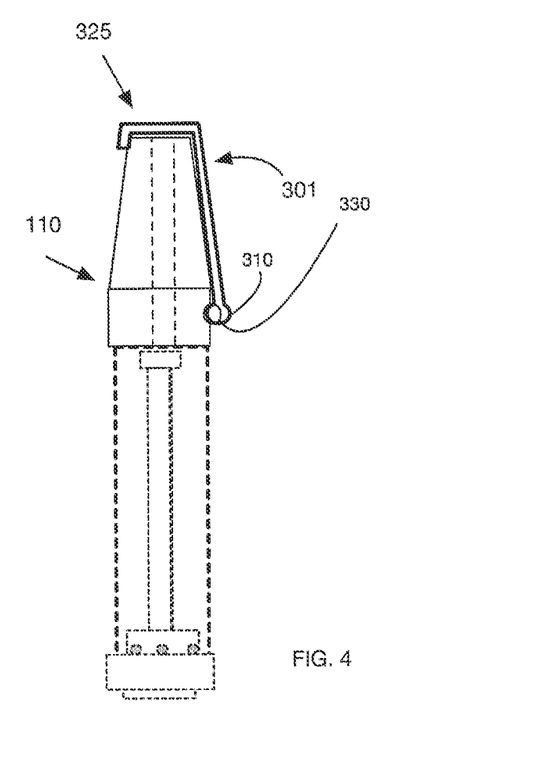
FIG. 4 show another flip top tamper resistant vaporizer cartridge.
Figure 5A:
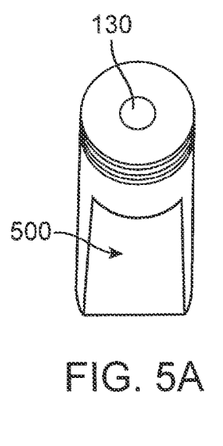
FIGS. 5A-5L illustrate aspects of latching flow control tamper resistant vaporizer cartridges.
Figure 5B:
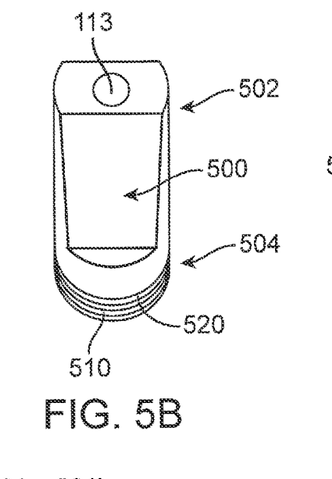
Figure 5C:
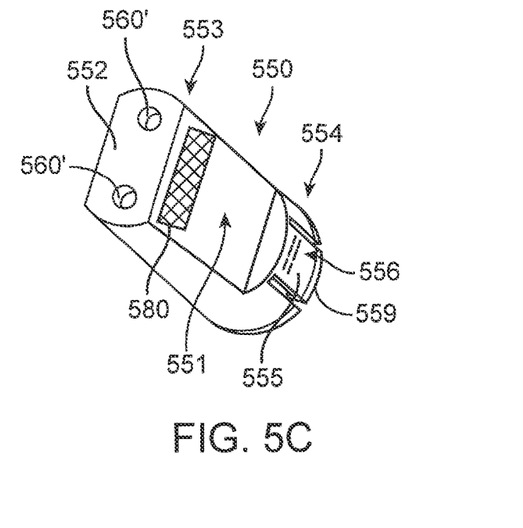
Figure 5D:
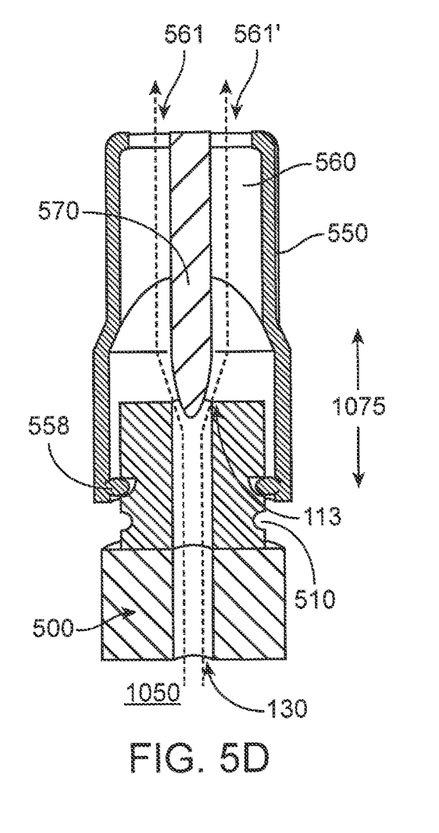
Figure 5E:
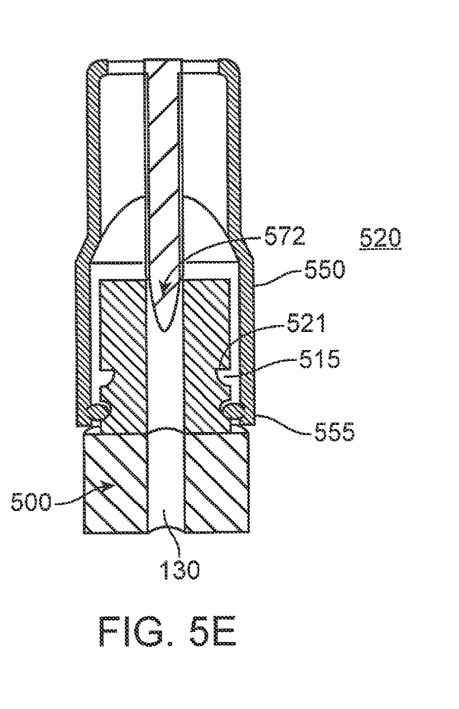
Figure 5F:
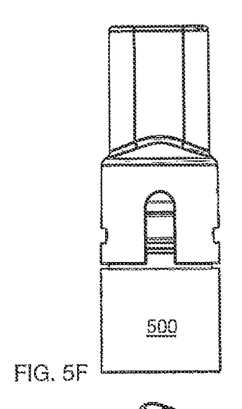
Figures 5G, 5H, 5I:
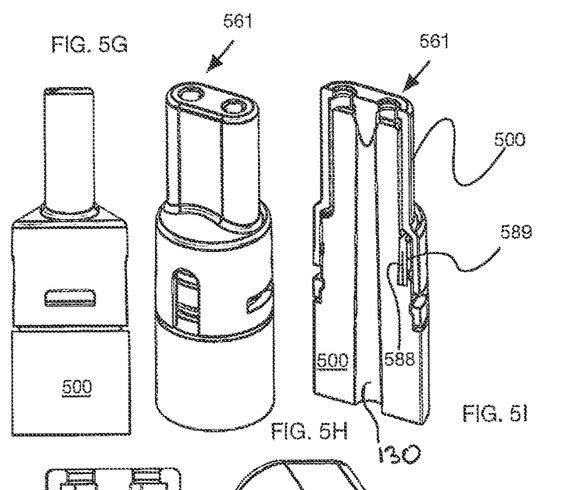
Figure 5J:
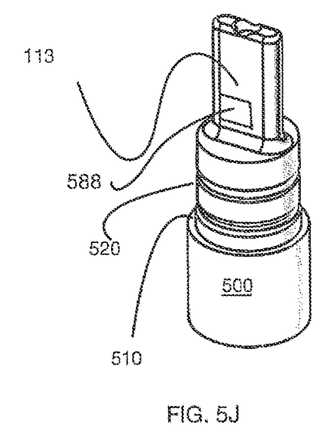
Figure 5K:
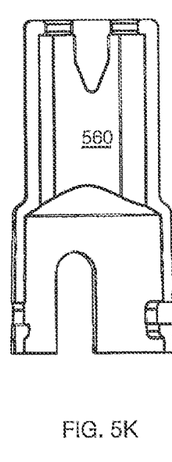
Figure 5L:
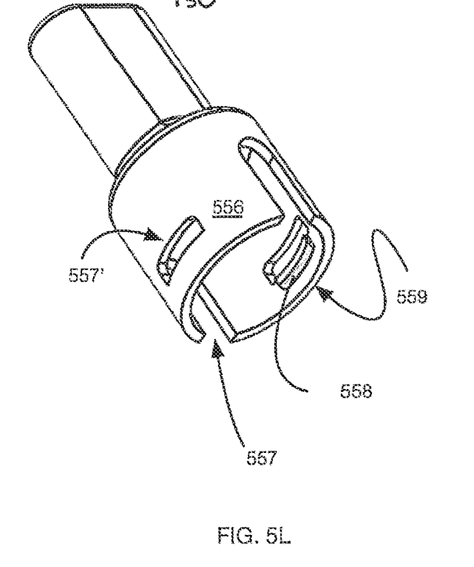

FIG. 4 shows a variation on the lip top device wherein a first portion 330 of the pivot 310 is formed as part of the tip and is configured to pressure fit into the flexible arm and the ring is eliminated.

FIGS. 5A through 5L and FIG. 6 illustrate axially extending latches on a cap which are configured to engage catches on a tip to limit movement of the cap and/or unintended usage of a vaporizer. FIGS. 5A through 5L illustrate a vapor barrier cap 550 connecting a tip 500 having a vapor pathway 115 formed therethrough, a proximal end 502 with an outlet 113 and a distal end 504. The distal end configured to mate with the tip connection 118 of a cartridge 100 (see FIG. 1) forming a fluid pathway from the cartridge to the tip. A barrier cap 550 is a generally hollow tube body 551 and a top 552 formed as part of the cap and partially covering the proximal end 553 of the tube body partially sealing the tube. The tube body 551 forms a vapor flow guide (VFG) 560 wherein vapor from an unblocked outlet 113 will flow. The VFG terminates into at least one inhalation port 561 and 561' which form an inhalation outlet whereby said vapor can flow along the line 1050. Inside the barrier cap is at least one plunger 570. The plunger is an extended leg which is configured to block the outlet 113 when moved into same. At the end of the plunger is a shaped plunger tip 572 that is configured to reversibly block said outlet.

An RFID tag or chip 588 may be added. A slot or cavity 589 for said RFID tag may be formed in one of the tip 500 or the barrier cap 550. Said RFID tag is configured to cooperate with a track and trace system for vaporizer cartridges.

The barrier cap 550 is configured to cooperate with the tip to facilitate limited movement of the barrier cap axially along the tip. Said movement requires a force that exceeds the force at least 70% of 5 year old children can exert. More preferable exceeds the force 90% of 5 year old children can exert and most preferably exceeds the force at least 95% of 5 year old children can exert.

Cap Movement

From the distal end of the barrier cap extend at least one moving latch wall 556 separated by a vertical flex guide 567. Each moving latch wall 556 and finger latch 558 is configured to face the center of said barrier cap. An additional horizontal flex guide 557' may be formed in the moving latch wall 556. The depiction of the flexible finger as a small area of the distal end of the cap is not a limitation and those of ordinary skill in the art will understand that the range of flexible fingers or wall sections may be a larger or smaller. The choice of material may impact the finger dimensions to achieve a predetermined latching force. flexible finger and latch are configured to reversible latch into catches formed on the tip. A section of the wall forms a moving latch wall 556, supporting a finger latch, is configured to bend without breaking if sufficient radial force is applied to the flexible finger latch. That moving latch wall 556 may be thinner, grooved or otherwise formed to act as a living hinge. In some instances the selected thickness of the wall adjacent to the moving latch wall and regions distance from the free end 559 of the moving latch wall 556 cooperate to limit finger latch 558 movement to correspond to a predetermined amount of force being applied. The first catch 510 is an annular extended ring or indentation around the distal end 504 of the tip. A second catch 520 is formed above the first catch near to the proximal end 502 of the tip and an interference member or region 515 is between the first and second catches. That region is formed as an annular section that may be indented or extended.

In operation the latch 558 and flexible finger 555 are shaped to be at rest (not under substantial radial stress) the first catch 510 is shaped to facilitate movement into and out of the catch in an axial and upward direction over the interference member 515 along the path of line 1075 to reach the second catch 520. The second catch 520 is shaped and configured to prevent upward movement of the latch 558. At least one shaped region 521 if the second catch forms a stop to restrict and limit removal of the barrier cap. The latch 558 may have a shape corresponding to the second catch. When the latch is in the second catch the barrier cap can normally only be moved downward along the path of arrow 1075 towards the distal end of the tip.

Vapor Blocking

The plunger 570 and plunger tip 572 formed inside the barrier cap cooperatively move along the same line as the barrier cap relative to the tip. When the barrier cap is fixed at the first catch the plunger tip block the outlet 113 of the tip. When the barrier cap is extended axially the barrier cap is lifted and the plunger no longer blocks the outlet 113. Accordingly, vapor can flow through the vapor flow guide (VFG) and exit the barrier cap via the at least one inhalation ports 561/561'. To restrict vapor flow and prevent unauthorized use by children and the like the vapor barrier cap should be moved back to the first catch position thereby blocking the outlet. Grasping features 580 such as rough areas, indentations, divots, bumps, grooves outdents and the like may be added to at least a portion of the barrier cap to facilitate gripping. The movement of the barrier cap relative to the tip requires a predetermined amount of force. In some instances the vapor barrier cap may be disposable as is the cartridge—the action of the flexible finger cooperating with the catches should provide for at least the number of use cycles said cartridge can supply. A use cycle is generally the number of consumer uses of the device. Generally speaking at least 60 movements between catch one and catch two (a cycle) for a 1 ml cartridge would be expected. More preferable about 75 cycles.

Figure 6:
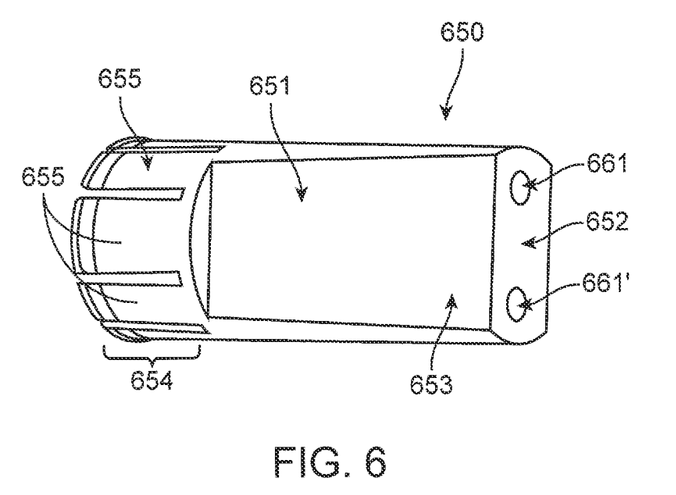
FIG. 6 illustrates aspects of a multi-latch flow control tamper resistant vaporizer cartridges.
Figures 7A, 7B:
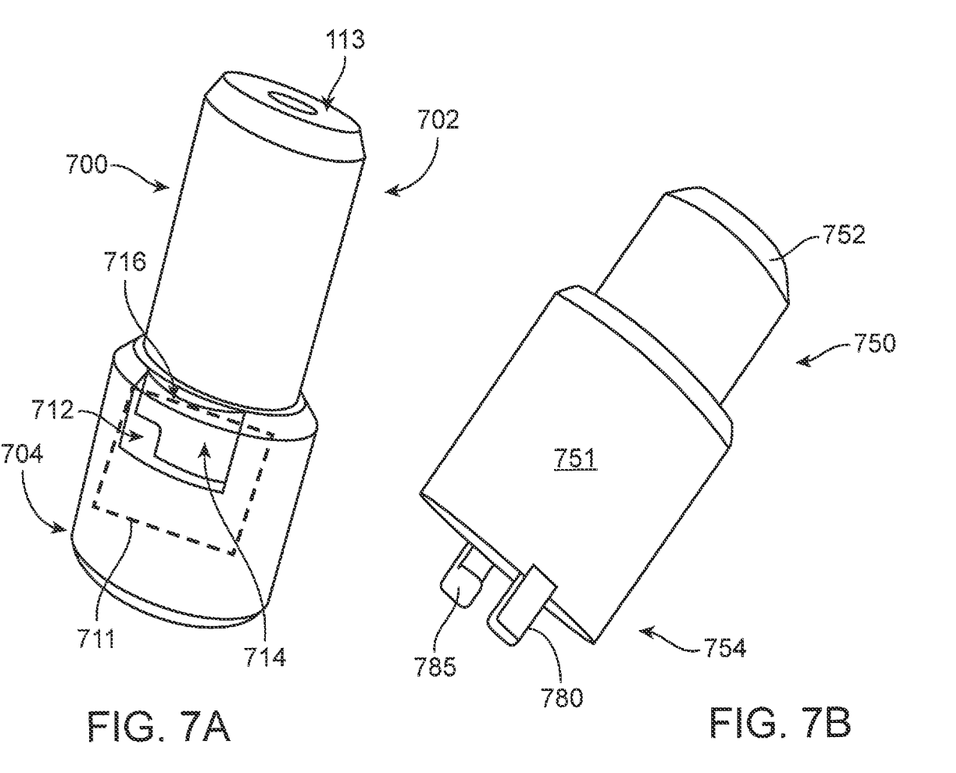
FIGS. 7A-7H illustrate aspects of rotating flow control tamper resistant vaporizer cartridge.
Figure 7C:
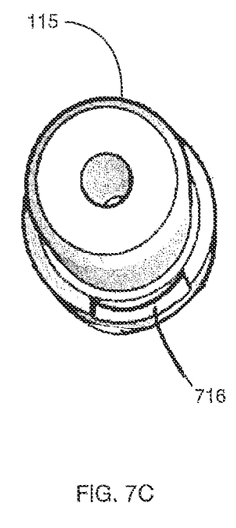
Figure 7D:
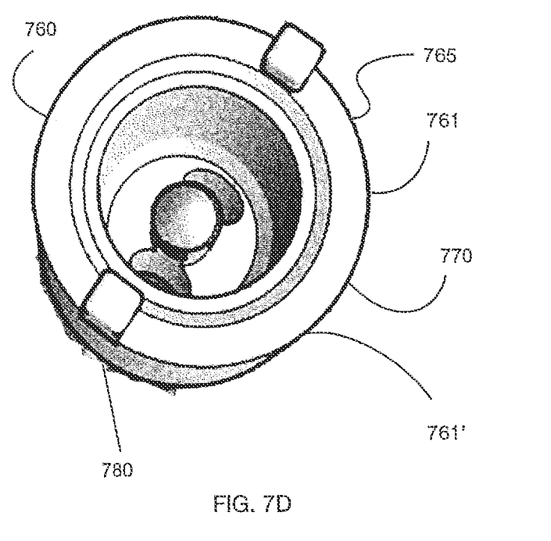
Figure 7E:
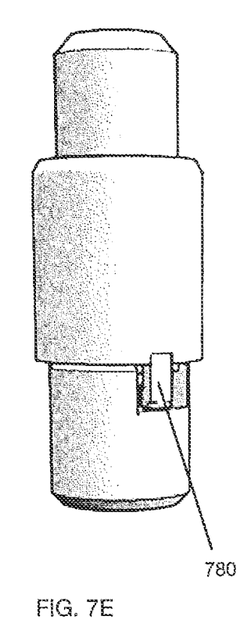
Figure 7F:
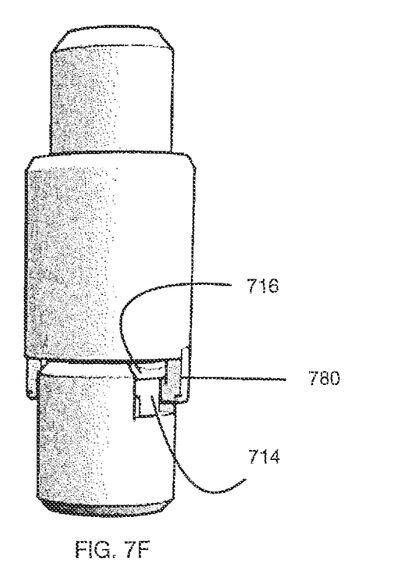
Figures 7G, 7H:
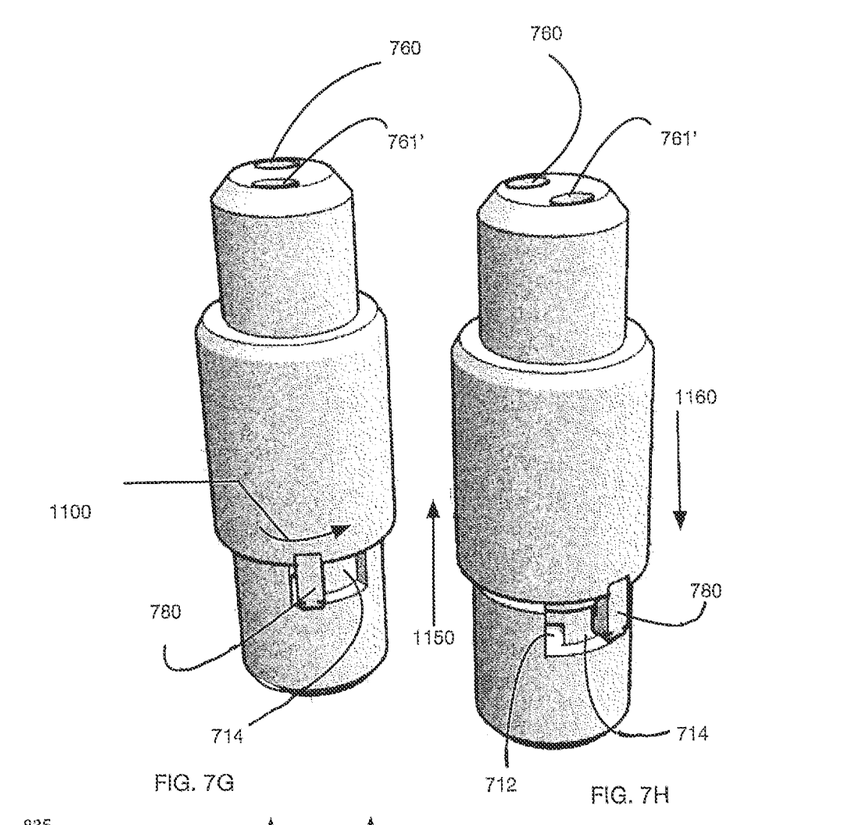

FIG. 6 illustrate another vapor barrier cap 650 configured to connect to tip 500. The multi-leg barrier cap 650 is a generally hollow tube body 651 and a top 652 over a proximal end 653 of the body partially sealing the body tube. A series of flexible finger 655 are formed around the distal end 654 of the cap. The tube body forms a vapor flow guide (VFG) wherein vapor from an unblocked outlet 113 will flow. The VFG terminates into at least one inhalation port 66i and 661' which form an inhalation outlet whereby said vapor can be inhaled. Inside the barrier cap is at least one plunger as described in reference to FIGS. 5A-5E and which functions as described above.

FIGS. 7A through 7H disclose a twisting vapor outlet tip 700 and a control cap 750. Axially extendable members formed as part of the cap are configured as latches to releasably engage a series of catches formed on the corresponding tip 700 thereby limiting movement of the cap and/or unintended usage of a vaporizer. The connecting tip 700 has a vapor pathway formed therethrough, a proximal end 702 with an outlet 113 and a distal end 704. The distal end is configured to mate with the tip connection end 118 of a cartridge 100 (see FIG. 1) forming a fluid pathway from the cartridge to the tip.

The control cap 750 is a generally hollow tube body 751 and a top 752 formed as part of the cap and partially covering the proximal end 752 of the tube body partially sealing the tube. The distal end 754 of the body terminates at a bottom edge 756. The tube body 751 has an inner annular wall 760 which forms a vapor flow guide (VFG) wherein vapor from an unblocked outlet 113 will flow. The VFG terminates into at least one inhalation port 761 and 761' which form an inhalation outlet whereby said vapor can flow along the line. Inside the control cap is at least one plunger 770. The plunger is an extended leg which is configured to block the outlet 113 when moved into same. At the end of the plunger is a shaped plunger tip 772 that is configured to reversibly block said outlet.

The control cap 750 is configured to cooperate with the tip to facilitate limited movement of the barrier cap axially along the tip. Said movement requires a force that exceeds the force at least 70% of 5 year old children can exert. More preferable exceeds the force 90% of 5 year old children can exert and most preferably exceeds the force at least 95% of 5 year old children can exert.

The control cap 750 has at least two flexible feet 780 extended from the distal end 754 of the control cap. Toe latches 785 extend inward from each of the flexible feet 780.

Cap Movement

The control cap moves radially and axially around the tip. Latches and catches formed between the toes and a series of catches and stops restrict the movement and set the force required to move the toes form one catch to another. Each toe 785 is configured to temporarily mate with catches. The catches and stop are formed in the catch section 711 of the side wall of the tip. A deep catch 712 is, as the name implies, deep. It extends inward radially further than other catches. The deep catch is configured to temporarily retain a toe 785 placed therein. The flexible feet 780 and toe 785 combination are removed from the deep catch by applying a rotational force along the line of arrow 1100. Sufficient force must be applied to the control cap to distort the flexible feet whereby the toe 785 can exit the deep well. When sufficient force is applied the toe is moved to the shallow well 714. Once in the shallow well the control cap may be lifted axially along the tip following line 1150 thereby lifting the plunger tip 772 out of the outlet 113. The shallow well extends upward closer towards the proximal end 752 of the control cap than the deep well does. At an upper boundary of the shallow catch a stop is formed and configured to inhibit removal of the control cap by prevent or limiting the toe from being displaced over it.

Vapor Flow

The fluid pathway is selectively closed and opened via the rotating and linear movement of the control cap relative to the tip. Lifting the control cap along arrow 1100 opens the fluid pathway inside the tip and cap system and allows vapor to flow from the outlet 113 into the VFG and eventually out of the at least one inhalation port. To close off vapor flow from the outlet the user reverses the steps and linearly pushes the control cap 750 downward towards the distal end of the tip 704 along the line of arrow 1160.

Figure 8:
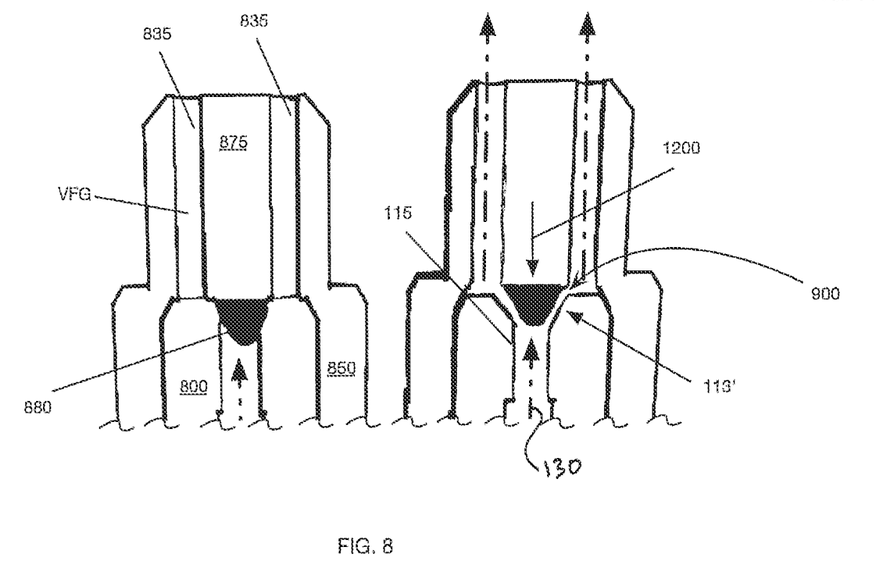
FIG. 8 illustrates aspects of flow control between a tip and cp.

FIG. 8 is a cut-away showing the open-close sequence of a tip 800 and cap cover 850 combination to allow or block vapor. The vapor pathway 130 terminates in an shaped outlet 113', the cap cover 850 is formed and configured to movable mate with the tip. The cap cover is substantially hollow and forms a vapor fluid guide VFG which terminates into at least one fluid pathway 835. A plunger 875 with a plunger tip 880 extend inside the cover cap towards the shaped inlet. The cap cover and tip cooperate to form a substantially sealed system wherein the plunger tip 880 is configured to temporarily seal or limit most of, the vapor pathway 130 when the cover cap is pushed down along the line of arrow 1200 thereby blocking vapor flow through the outlet to VFG interface 900.

Figures 9, 10:
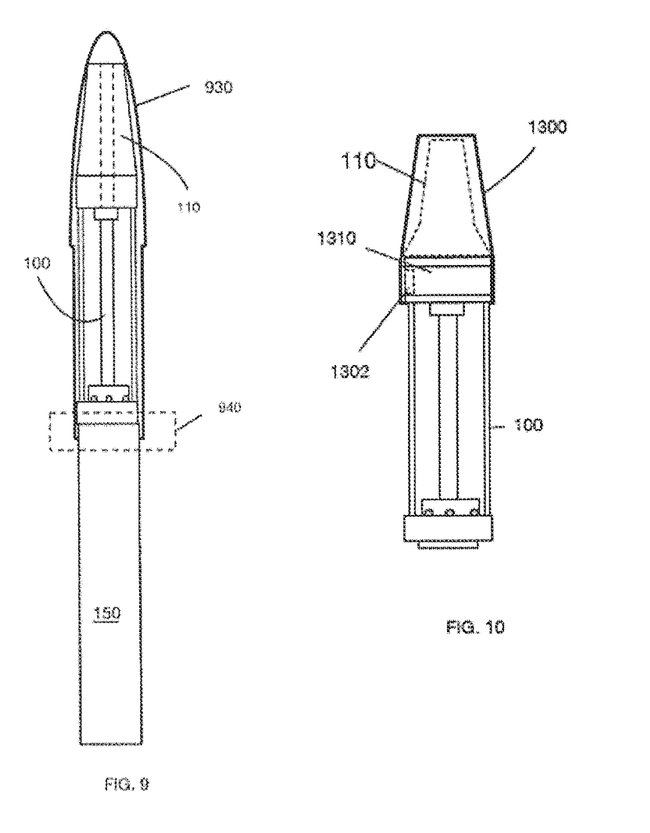
FIG. 9 illustrates a sheath utilizing a snap-on resistant vaporizer lock.
FIG. 10 illustrates a magnetic latch cap for a resistant vaporizer lock.

FIG. 9 shows aspects of a sheathed vaporizer pen with a base 150 connected to a cartridge 100 having a tip 110 covered by a vapor blocking sheath 930 which mates with the body at an interface 940. The interface represents the latch and catch systems taught in FIGS. 2A-2D.

Figure 11:
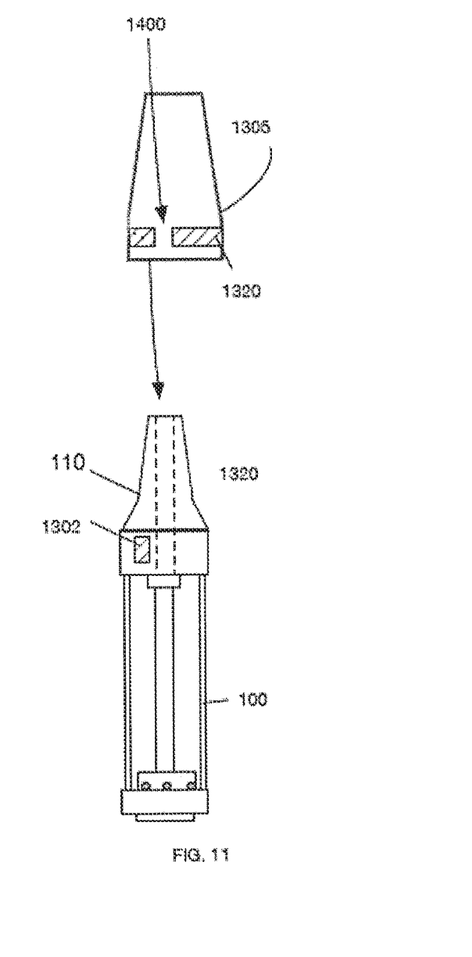
FIG. 11 illustrates a magnetic latch cap for a resistant vaporizer lock.
Figures 12A, 12B, 12C, 12D, 12E, 12F:
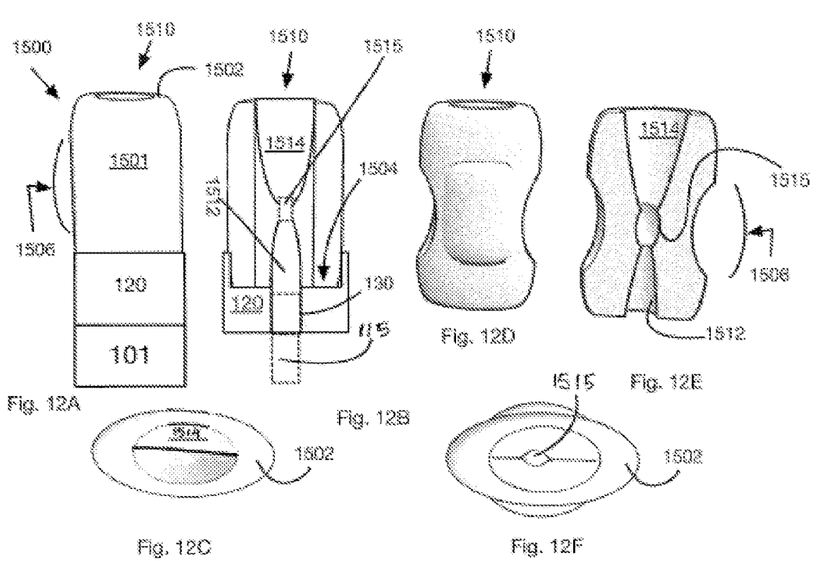
FIGS. 12A-12F illustrate a sequence of opening a squeeze valve tip.
Figure 13A:
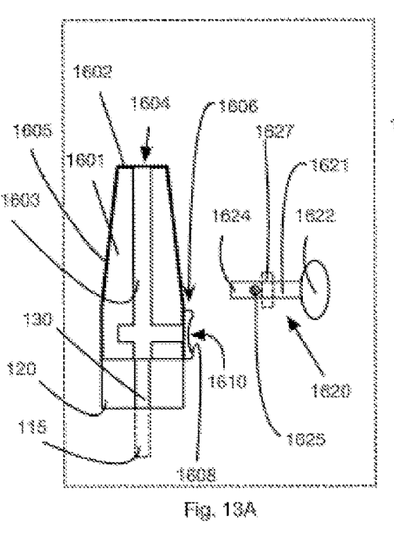
FIGS. 13A-13E illustrate a turn valve tamper proof tip and a sequence of opening a fluid pathway in the tip.
Figure 13B:
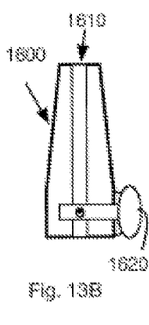
Figures 13C, 13D:
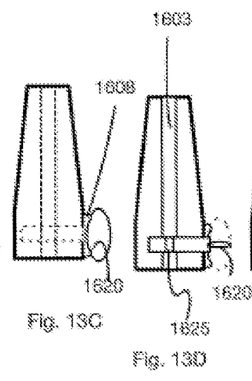
Figure 13E:
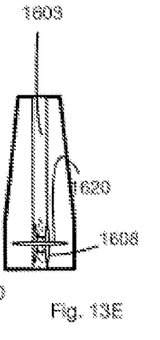

FIGS. 10 and 11 shows aspects of magnetic latch systems for a tamper resistant vaporizer cartridge and tip. In FIG. 10 a permanent magnet 1302 is affixed, embedded and/or attached to a tip 110. A cover 1300 that has at least a metallic section 1310 (however those of ordinary skill in the art will recognize the entire cover may be magnetic). When the magnet and metallic section are aligned the magnet embedded in the tip restricts removal of the cap unless sufficient force is applied. The magnet has a sufficient magnetic field to restrict removal by a predetermined age child in accordance with applicable codes and regulations as previously noted.

In FIG. 11 a permanent magnet 1302 is affixed and/or embedded or attached to a tip 110. A cover 1305 has a metallic section 1320 with a gap 1400 formed therein. The gap forms a passageway by which the cap may be removed. However, when the magnet and metallic section are aligned the magnet embedded in the tip restricts removal of the cap unless sufficient force is applied to rotate the cap around the tip and align the gap to magnet. The magnet has a sufficient magnetic field to restrict the movement by a predetermined age child in accordance with applicable codes and regulations as previously noted.

FIGS. 12A-12FA illustrate a device and method of method of selective blocking and unblocking vapor flow through a tip. The squeeze tip disclosed herein as a portion of the tip which is deformable to temporarily open a fluid pathway through said tip. The pressure required to open said pathway is predetermined to exceed that of what at least 90% of five year olds can exert. Most preferable to exceed a pressure that at least 95% of five year olds can achieve.

The method and device teach a linear vaporizer cartridge 100 configured to mate with a power supply having a first end 102 with a vapor pathway 115 fluidly open to a tip connection 118. The soft tip 1500 has a vapor inlet/pathway 130 through its distal end 120 which fluidly connects with the vapor pathway 115. The tip has a body 1501 with a top end 1502, bottom end 1504 and flexible side walls 1506 surrounding a fluid pathway formed within a pliable or soft rubber-like material forming at least a portion of the tip. Within the soft tip section is formed a first half pathway 1512 fluidly connected to a second half pathway 1514 via a deformable valve 1515. The second half pathway is fluidly connected to an inhalation outlet 1510. The deformable valve 1515 is configured to open and close in response to pressure which deforms the soft tip and opens the valve. The soft tip is formed in a closed or blocking state when at rest which may be referred to as a sealed state. Operation of the valve is accomplished by exerting sufficient pressure on the sides of the soft tip via squeezing the side walls. A predetermined squeeze force deforms open the valve 1515 thereby allowing vapor produced by a cartridge fluidly connected to the tip to will flow through the first and second half pathways.

To provide child protection the predetermined force is a force that is at least too great for at least ninety percent of five year old to overcome. More preferably the predetermined force is a force that is too great for at least ninety-five percent of five year old to overcome.

FIGS. 13A-13E illustrate a device and method of method of selective blocking and unblocking vapor flow through a tip. The stem valve disclosed herein is a rotatable fixture configured to twist under a predetermined torque whereby one or more rotation limiting fixtures on the side edge of the cartridge 1605 prevent opening the fluid pathway through the tip unless adequate torque is supplied. a linear vaporizer cartridge 100 configured to mate with a power supply having a first end 102 with a vapor pathway 115 fluidly connected to a tip connection 118. The tip 1600 has a vapor inlet/pathway 130 through its distal end 120 which fluidly connects with the vapor pathway 115.

The tip 1600 has a body 1601 and a series of fluid connections therein. At a proximal end 1602 an outlet 1604 is configured which is fluidly connected to a valved pathway 1603. On a portion of the outer annular wall 1605 of the tip at least one fixture forming a force limiting rib (FLR) 1606 is formed. Each FLR is a shaped plastic with adequate memory to flex and return to there at rest position thereafter. The flexible protruding rib(s) has shaped extended arms 1608 configured to require a predetermined amount of force to bend. The FLRs are positioned adjacent to a valve stem guide 1610. The valve stem 1620 is configured to mate with the stem guide in a rotatable fashion. The interface of the valve stem to the stem guide should be snug whereby the valve stem can rotate but will also block the valved pathway 1603 when in the closed position. At the distal end 120 of the tip a vapor pathway 130 is connected to the outlet 1604. The valve stem 1620 has an elongated body 1621, a stem proximal head 1622, a distal stem end 1624, and a valve connect 1625 configured to mate within the stem guide and block the fluid pathway in a first configuration and unblock the fluid pathway in a second configuration. In the first configuration the valve connect is closed and perpendicular to the valved pathway 1003. In the second or open configuration the valve connect is aligned with the valved connect thereby allowing vapor flow.

In operation a user grasps the stem proximal head 1622 which, in the first configuration is closed, and exerts sufficient torque on the valve stem to rotate the proximal head past the FLR extended arms 1608 (which are flexible and will, under sufficient force, bend to allow passage of the proximal head). The twisting aligns the valve connect to the second thereby allowing vapor to flow through the valved pathway. Closing the valved pathway is achieved by reversing the above process/method of operation wherein the stem proximal head can be turned past the FLR be a predetermined amount of rotational force or torque.

The predetermined force to overcome the arm of the FLR is at least a force that is too great for at least ninety percent of five year old to overcome. More preferably the predetermined force is a force that is too great for at least ninety-five percent of five year old to overcome.

It will be understood that various aspects or details of the disclosures may be changed combined, or removed without departing from the scope of the invention. It is not exhaustive and does not limit the claimed inventions to the precise form disclosed. Furthermore, the foregoing description is for the purpose of illustration only, and not for the purpose of limitation. Modifications and variations are possible in light of the above description or may be acquired from practicing the invention. The claims and their equivalents define the scope of the invention.

What is claimed is:

1. A method of selective blocking and unblocking vapor flow through a tip, the method comprising:
   providing an extract containing vaporizer cartridge (100) configured to mate with a power supply at a first end (102) and with a vapor pathway (115) fluidly connected to a tip connection (118);
   a tip (1500), configured to having a body (1501), top end (1502), bottom end (1504) flexible side walls (1506) surrounding a fluid pathway comprising;
   a first half pathway (1512) fluidly connected to the vapor inlet/pathway (130) through the distal end (120) of the tip;
   a second half pathway (1514) fluidly connected to an inhalation outlet (1510);
   a deformable valve (1515) in a sealed state when at rest; and,
   wherein squeezing the side walls with a predetermined force deforms and opens the deformable valve thereby allowing vapor produced by the cartridge fluidly connected to the tip to flow through the first and second half pathways.

2. The method of claim 1, wherein the predetermined force is a force that is too great for at least ninety percent of five year old to overcome.

3. The method of claim 1 wherein the predetermined force is a force that is too great for at least ninety-five percent of five year old to overcome.

4. A method of selective blocking and unblocking vapor flow through a tip, the method comprising:
   providing a linear vaporizer cartridge (100) configured to mate with a power supply at a first end (102) and with a vapor pathway (115) at a second end (118);
   connecting a tip (500) having a vapor pathway (130), proximal end (502) with a vapor outlet (113) and a distal end (504) to the second end forming a fluid pathway from the vapor outlet to the vapor pathway;
   opening the vapor pathway through of the tip by pulling a barrier cap (550) axially from the second end towards the top (551) of the barrier cap thereby displacing one or more flexible fingers (555) formed at the distal end (554) of the barrier cap from a first at rest position in a first catch (510) over an interference member (515) and into a second position in a second catch (520) thereby unblocking the outlet (113) by moving a plunger (570) extending downward axially from the barrier cap top (551) and within the barrier cap from blocking the outlet (113);
   wherein vapor can flow through the vapor flow guide (VFG) (560) formed by the barrier cap and be drawn out of one or more inhalation ports (561 and 561'); and,
   wherein a predetermined force is required to displace the flexible finger over the interference member.

5. The method of claim 4 wherein the predetermined force is a force that is too great for at least ninety percent of five year old to overcome.

6. The method of claim 4 wherein the predetermined force is a force that is too great for at least ninety-five percent of five year old to overcome.

7. The method of claim 4 wherein the second catch has at least one shaped surface (521) configured to prevent removal of the at least one flexible finger by the force necessary to move the fingers from the first catch over the interference member and into the second catch.

8. The method of claim 4, the method further comprising pressing on the barrier cap towards the distal end (554) of the vaporizer cartridge wherein the fingers (555) move from the second catch to the first catch and block the vapor pathway (115).

9. A fixed cap that selective blocks vapor flow through a tip, comprising: a tip (500) having a vapor pathway (130), proximal end (502) with an outlet (113) and a distal end (504); a first catch (510) formed radially around the distal end of the tip; a second catch (520) formed radially around the distal end of the tip; an interference member (515) between the first and second catches; a barrier cap (550) with a top (551) having and a distal end (554); a plunger (570) extending downward axially from the top (551) within the barrier cap; at least one flexible leg (555) formed at the distal end of the barrier cap configured to latch with the catches; wherein a fluid pathway is opened through the barrier cap from the tip through one or more inhalation ports (560 and 560'); and, wherein a predetermined force is required to displace the leg over the interference member.

10. The method of claim 9 wherein the predetermined force is a force that is too great for at least ninety percent of five year old to overcome.

11. The method of claim 9 wherein the predetermined force is a force that is too great for at least ninety-five percent of five year old to overcome.

* * * * *